US006416978B1

(12) United States Patent
Lee et al.

(10) Patent No.: US 6,416,978 B1
(45) Date of Patent: Jul. 9, 2002

(54) EXOPOLYSACCHARIDE PRODUCTION FROM SUBMERGED MYCELIAL CULTURE OF MUSHROOM

(75) Inventors: Shin-Young Lee, 102-707, Bobae Apt., Ohneui-dong, Chunchon-si 200-190, Kangwon-do; Kyu-Min Lee, Seoul, both of (KR)

(73) Assignees: MBiotech Co., LTD; Shin-Young Lee, both of (KR)

( * ) Notice: Subject to any disclaimer, the term of this patent is extended or adjusted under 35 U.S.C. 154(b) by 0 days.

(21) Appl. No.: 09/697,163

(22) Filed: Oct. 27, 2000

(51) Int. Cl.[7] ............................. C12P 19/04; C12P 1/02; C12N 1/14
(52) U.S. Cl. .................... 435/101; 435/171; 435/254.1; 435/911
(58) Field of Search .............................. 435/101, 254.1, 435/911, 171

(56) References Cited

PUBLICATIONS

Lee, K. et al., "Effect of Ammonium Phophate on Mycelial Growth and Exopolysaccharides Production of *Ganoderma lucidum* in an Air–Lift Fermenter", Journal of Microbiology and Biotechnology, vol. 9, pp. 726–731, (1999).

Lee, K. et al., "Bistage Control of pH for Improving Exopolysaccharides Production from Mycelia of *Ganoderma lucidum* in an Air–Lift Ferment", Journal of Bioscience and Bioengineering, vol. 88, No. 6. pp. 646–650, (1999).

*Primary Examiner*—Herbert J. Lilling
(74) *Attorney, Agent, or Firm*—Finnegan Henderson Farabow Garrett & Dunner, L.L.P.

(57) ABSTRACT

This invention relates to a process for producing exopolysaccharide from submerged mycelial culture of mushroom and more particularly, to the process for improving the exopolysaccharide production from the mycelia using the different bistage pH control technique comprising the steps of; (1) a process for the production of mycelia whose pH conditions in a batch medium are kept constant at 2 to 6 at the initial pH, while adding ammonium ion to the medium, and (2) a process for the production of exopolysaccharides whose pH conditions in a batch medium containing the mycelia are adjusted to 3 to 7. According to this invention, the optimized mycelial morphology and rheological properties in the culture media can lead to EPS production in more efficient and stable manner.

6 Claims, 17 Drawing Sheets

A: Medium containing no ammonium ion

B: Medium containing ammonium ion

EXOPOLYSACCHARIDE PRODUCTION FROM SUBMERGED MYCELIAL CULTURE OF MUSHROOM

BACKGROUND OF THE INVENTION

1. Field of the Invention

This invention relates to a process for producing exopolysaccharide from submerged mycelial culture of mushroom and more particularly, to the process for improving the exopolysaccharide production from the mycelia using the different bistage pH control technique comprising the steps of; (1) a process for the production of mycelia whose pH conditions in a batch medium are kept constant at 2 to 6 at the initial pH, while adding ammonium ion to the medium, and (2) a process for the production of exopolysaccharides whose pH conditions in a batch medium containing the mycelia are adjusted to 3 to 7.

2. Description of the Related Art

Mushrooms have attracted a great deal of interest in many areas of foods and herbal drugs, etc. The main components used for biological applications are polysaccharides, which exists within the mushrooms or in its secretion. Recently, the study of exopolysaccharides (EPS) has been conducted extensively, since their production processes from culture broth do not require extra steps and they require relatively simple purification processes. However, it has been very difficult to culture large amounts of mycelium in a large-scale fermentor in order to produce reasonable amounts of EPS. There have been several limitations in scaling-up the mycelial culture system due to its low secretion level and changes in the physical properties of the culture broth such as viscosity, morphology, etc. A major problem in cultivating the mycelium is the increase of viscosity of culture broth when the mycelium grows, which results not only in limiting oxygen transfer, but also in building up shear stress. High shear stress has a negative effect on the morphology of the mycelium which can directly reduce the cell growth along with EPS production. No attempts have been made to show the effect of adding ammonium ion in previous work, even though the mycelial cells were grown in ammonium ion containing medium. For filamentous fungi, it is well known phenomenon that cell growth was increased by adding ammonium ions, possibly due to their role of facilitating carbon accumulations. However, a repressive effect of excessive ammonium ions on antibiotic production has also been reported.

Meanwhile, *Ganoderma lucidum* belongs to family Polyporaceae and its fruiting bodies are called *Ganoderma lucidum*. Hitherto, it has been proved to have various therapeutic efficacies such as antihypertension, diuresis, cardiac stimulation, cardiotonic, etc. In an effort to produce *Ganoderma lucidum*, the solid cultivation method using saw or lumber has been mainly applied in a farmhouse, but the conventional method has some drawbacks because a longer cultivation time is required with intensive labor and the extraction process of polysaccharides from the fruiting bodies has met with difficulty.

To comply with this matter, a batch cultivation method has been widely used with the following advantages: (1) cultivation can be made available under constant conditions at all times, (2) the mycelium of homogeneous quality can be obtained in high yield and with large-scale production, and (3) the production cost is reasonable. However, the batch cultivation method for industrial use has recognized some disadvantages in that its extraction process for polysaccharides ($\beta$-1,3-glucan of antitumor activity), active ingredient of *Ganoderma lucidum*, from the mycelium is very complicated and its yield is quite low.

Further, unlike the intensive studies for lower bacteria, the morphological and rheological studies for higher bacteria such as *Ganoderma lucidum* belonging to family Polyporaceae have yet to be elucidated during the batch cultivation, and the correlation between Polyporaceae and EPS production has not been reported. More specifically, it is important to make intensive studies on the correlation for a large-scale EPS production. In particular, to ensure the stability and productivity of the EPS, the changes in morphological and rheological parameters should be connected to mycelial concentration and their products, while cultivating the mycelium with different cultivation conditions. Currently, there is an urgent need for the research of various factors related to *Ganoderma lucidum* (e.g., pH, nitrogen source, mycelial morphology and rheological parameters, correlation between cell growth and EPS production).

SUMMARY OF THE INVENTION

To overcome the aforementioned shortcomings, the inventor et al. have conducted intensive studies that since the optimal conditions of both mycelial growth and EPS production are different each other, the EPS production is effectively improved in such a manner to optimize the cultivation conditions in the batch medium depending on each of desired products. Thus, this invention has been completed.

Therefore, an object of this invention is to provide a large-scale EPS production using the different bistage pH control technique from the mycelial production and EPS production.

BRIEF DESCRIPTIONS OF THE DRAWINGS

DETAILED DESCRIPTION OF THE INVENTION

Figure 1:
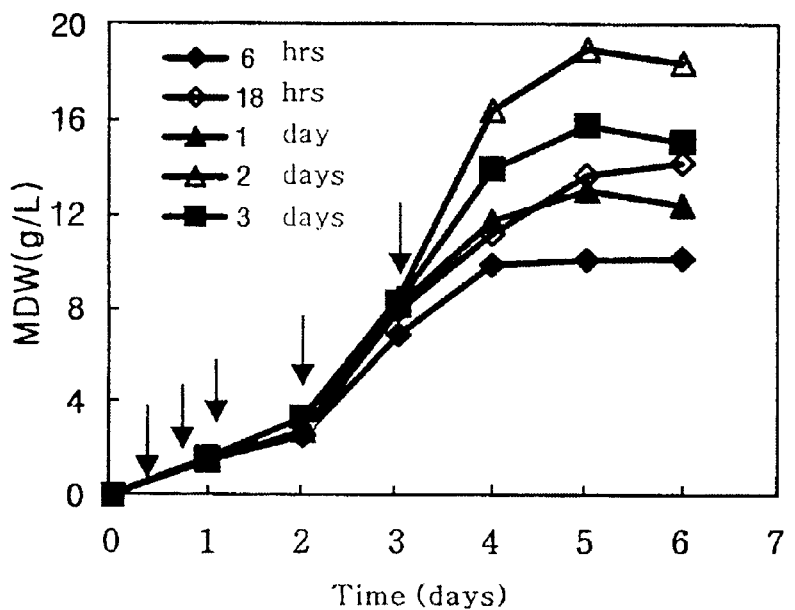
FIG. 1 is a graph showing the effect of bistage pH control on the mycelial dry weight (MDW), when the pH in the batch medium is shifted from 3 to 5.
Figure 2:
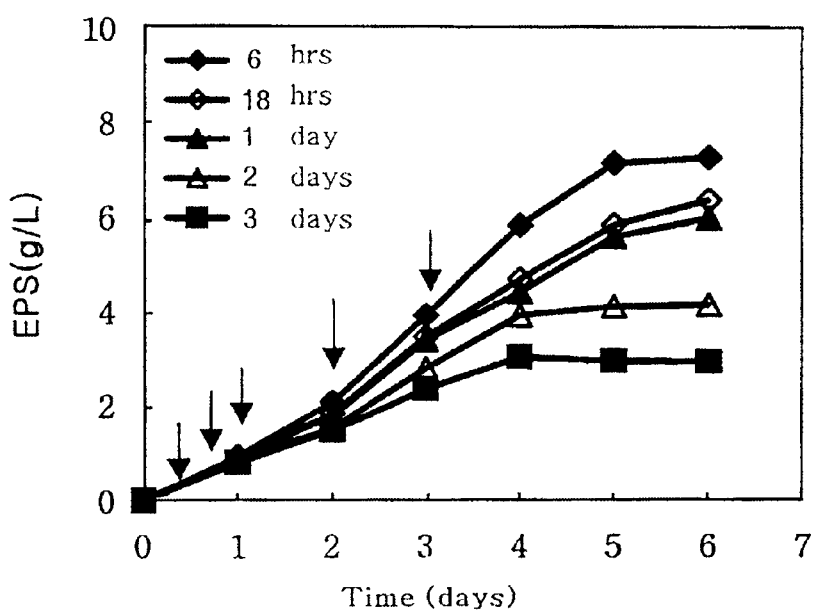
FIG. 2 is a graph showing the effect of bistage pH control on the EPS, when the pH in the batch medium is shifted from 3 to 5.

This invention relates to a process for producing EPS from the mycelia using the different bistage pH control technique comprising the steps of; (1) a process for the production of mycelia whose pH conditions in a batch medium are kept constant at 2 to 6 at the initial pH, while adding ammonium ion to the medium, and (2) a process for the production of exopolysaccharides whose pH conditions in a batch medium containing the mycelia are adjusted to 3 to 7.

According to this invention, the large-scale EPS production method is discribed in more detail as set forth hereunder.

The first step of this invention comprises the mycelial production method.

The typical examples of Ganoderma used for this invention include *Ganoderma lucidum, Ganoderma applanatum, Ganoderma tsugae, Ganoderma neo-japonicum*, or all Polyporaceae belonging to Ganoderma. These strains are cultured in the batch medium at pH 2–6, preferably at pH 3–4. If the pH range is less than 2 in the medium, high values of pH negatively affect both cell growth and EPS production. However, in the case of exceeding pH 6, cell growth is inhibited while EPS production is also decreased. The pH conditions in the medium can be kept constant by adding NaOH at the initial cultivation or during cultivation.

Hence, the excessive use of NaOH for the pH control may lead to the mycelial lysis. Thus, it is preferred that the amount of NaOH should be employed to maintain the level of pH 7. According to this invention, the batch medium may selectively contain 0.01~5 wt. % of ammonium ion because the presence of ammonium ion may greatly affect the rheological parameters of the culture system, such as consistency index and flow index, during cultivation.

The second step of this invention comprises the EPS production method.

NaOH is added to the medium containing mycelia obtained from the above optimized process and cultured at pH 3–7, more preferably at 5–6, unlike the first step of mycelial growth. Hence, if the pH range in the medium is less than 3, the increased apparent viscosity and reduced oxygen transfer necessary for respiration of mycelia may adversely affect EPS production. However, in the case of exceeding pH 7, the mycelium may be lyzed. The pH conditions in the medium can be kept constant by adding NaOH at the initial cultivation or during cultivation and then, the cultivation continues. Hence, the excessive use of NaOH for the pH control may lead to the mycelial lysis. Thus, it is preferred that the amount of NaOH should be employed to maintain the level of pH 7.

Meantime, ammonium ion in the medium plays an important role in both growing mycelium and producing EPS from *Ganoderma lucidum*. In lower concentration levels of ammonium ion (0–11 g/L), the mycelium maintains more filamentous morphology but it becomes changed into pellet morphology in high concentrations (5–11 g/L).

Further, filamentous mycelium is observed due to limitation of nutrient transfer during the cultivation at low concentration of ammonium ions contained in medium. On the other hand, the best EPS production is observed in medium with absence or low concentration of ammonium ions.

The rheological characteristics of culture broth and filtrate work well with Herschel-Bulkley model. The morphological changes of the mycelium resulting from the ammonium ion concentration directly affect the rheological characteristics of the culture system and results in reversely affecting the EPS production levels.

Meantime, an air-lift fermentor has often been employed to solve the shear stress problem of the conventional jar fermentor in maintaining a high density of the mycelia within short periods. According to this invention, the bistage pH control technique is applied to an air-lift fermentor, by which one pH value for optimal mycelial growth is shifted to an other value for enhancing EPS production.

Based on these results, therefore, this invention has an advantage in obtaining optimal mycelial growth and EPS production through careful regulation of the ammonium ion concentration in the culture media along with the review of correlation between rheological parameters and morphological characteristics of the mycelium.

This invention is explained in more detail based on the following examples and experimental examples. These examples are only designed to explain this invention in more detail, and the fact that this invention is not confined to the following examples and experimental examples will be obvious to those who have a common knowledge in the field to which this invention pertain.

EXAMPLE 1

Bistage Cultivation (1)

*Ganoderma lucidum* ASI 7004 was used as a stock culture of this invention and maintained on potato dextrose agar (PDA) plate at 30° C. for 7 days, and preserved at 4° C. This strain was subcultured every three months prior to use for this experiment. The grown mycelium was prepared in the form of mycelium disks using a stainless steel pipe having 5 mm in diameter. The 4 or 5 disks were inoculated into a 250 ml triangle flask containing 50 ml medium. The mycelium was cultured at 30° C. for 7 days, and 5%(v/v) pre-culture solution was again inoculated into a 250 ml triangle flask containing 50 ml seed culture medium. The culture was vigorously shaken at 100 rpm at 30° C. for 5 days. Then, the pre-culture solution was maintained by a homogenizer (Dongyang, model No. 0820) for 30 seconds and used for inoculation of this culture. The pre-culture solution was newly prepared for each experiment afterwards. Hence, the pre-culture medium used for the seed culture was a *Ganoderma applanatum* containing medium for vigorous shaking, which was used by Sone et al. [Sone, Y., Okuda, R., Wada, A., Kishida, A. and Misaki, A., *Structures and Antitumor Activities of the Polysaccharides Isolated from Fruiting Body and the Growing Culture of Mycelium of Agricultural Biological Chemistry*, 49(9), 2642–2650(1985)]. The seed culture was grown in an optimized medium containing glucose, 60 g/L; yeast extract, 6 g/L; $KH_2PO_4$, 0.5 g/L; $(NH_4)_2HPO_4$, 1 g/L; this medium was reported by Lee et al. [Lee, S. Y., Kang, T. S. and Lee, M. C., Condition of Exo-polysaccharide Production from Submerged Mycelial Culture of *Ganoderma lucidum* by Using Air-lift Fermenter System, *Kor. J. Biotechnol. Bioeng.*, 13(5), 1~7(1998)]. This medium was sterilized under the pressure at 121° C. for 15 minutes. The fermentor was a 3 L air-lift fermentor (working volume: 2 L) manufactured directly by the above Lee et al. under the following culture conditions: inoculation volume (5%, v/v), temperature (30° C.) and air ventilation rate (2.5 vvm). Hence, the fermentor was a concentric draught-tube internal loop type which can greatly reduce shear stress as compared with the conventional jar fermentor, and the sparger is a cylindrical ceramic type. The evaporated medium was condensed and recycled to the fermentor via an attached condenser.

The initial pH in the medium was adjusted to 3 with NaOH. After the seed strain was cultured at the time intervals of 6, 8, 24, 48, and 72 hours, the initial pH was increased to 6 for continuous cultivation. Then, mycelial dry weight (MDW) and crude EPS were assayed every 24 hours for 6 days. The results were shown in FIG. 1. The maximum level of MDW was 18.4 g/L, while the crude EPS was 7.27 g/L. Hence, to measure the MDW, the sample collected from the fermentor was centrifuged at 10,000× g for 15 minutes. The precipitate was washed with a filter paper (No. 2, Advantec) and distilled water two or three times, dried at 70° C. for 24 hours and left in a desiccator until the constant volume was reached. Then, the cell dried weight was obtained. Further, to measure the dry weight of EPS, the culture broth was centrifuged at 10,000× g for 15 minutes. After removal of mycelium, the culture filtrate was added two-fold volume of acetone over the culture broth, and the precipitate was obtained. The precipitate was dried at 70° C. for 24 hours to measured the dried weight.

EXAMPLE 2

Bistage Cultivation (2)

Figure 3:
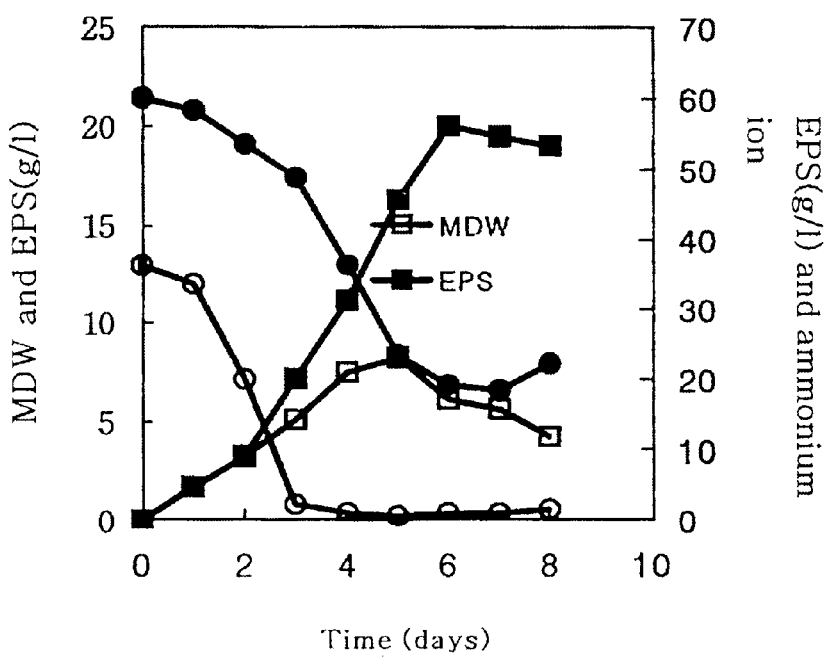
FIG. 3 is a graph showing the effect of bistage pH control on the MDW and EPS, when the pH in the batch medium is shifted from 3 to 6 after 6-hour cultivation.

The mycelium and EPS were cultured and assayed in the same manner as Example 1, except for the fact that 13 mg/L of ammonium ion was added to the medium and 6 hours after cultivation, the pH condition was adjusted to 6. The results were summarized in FIG. 3. The maximum level of MDW was 8.23 g/L, while that of EPS was 20.04 g/L.

EXAMPLE 3

Bistage Cultivation (3)

Figure 4:
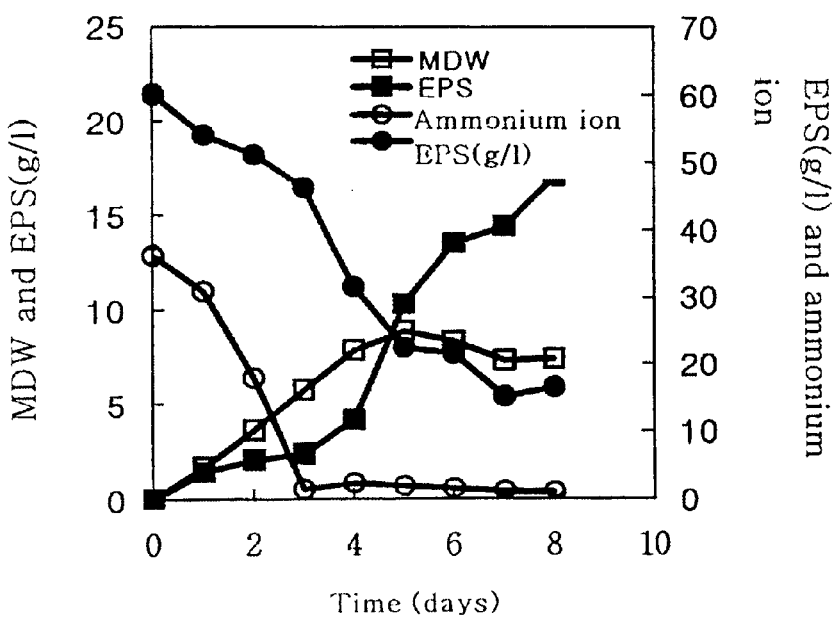
FIG. 4 is a graph showing the effect of bistage pH control on the MDW and EPS, when the pH in the batch medium is shifted from 3 to 6 after 2-day cultivation.

The mycelium and EPS were cultured in the same manner as Example 2 and assayed in the same manner as Example 2, except for the fact that after 2-day cultivation, the pH condition was adjusted to 6. The results were summarized in FIG. 4. The maximum level of MDW was 8.89 g/L, while that of EPS was 17.03 g/L.

From Examples 2 and 3, it was noted that when the pH conditions were changed after 6-hour and 2-day cultivations, the cell growth was increased until 5 days (8.23 g/L and 8.89 g/L) and reduced thereafter, showing the similar pattern as in the case of controlled pH. Compared to FIG. 1, the MDW was decreased by 81% and 49%, respectively. In particular, it was observed that when the mycelium was cultured at pH 3 for 6 hours and the pH value was increased to 6, maximum EPS production (20.04 g/L) was made available. When the controlled pH was constantly maintained at 6, the EPS production was enhanced about 1.28 times as high as that of Example 5 (15.71 g/L). Both Examples indicated that the ammonium ion concentration was sharply decreased and nearly depleted after 3-day cultivation; at this point, the glucose concentration was sharply decreased, while the EPS production was significantly enhanced. However, it was observed that the cell growth rate was decreased due to depletion of ammonium ion and with the addition of excessive amount of NaOH, the MDW was reduced due to cell lysis. On the other hand, the EPS production rate was increased when the ammonium ion concentration began to decrease. Thus it was deduced that the presence of ammonium ion in the culture media may lead to inhibition of EPS production.

EXAMPLE 4

Effect of Initial pH in the Medium Containing No Ammonium Ion

Figure 5A:
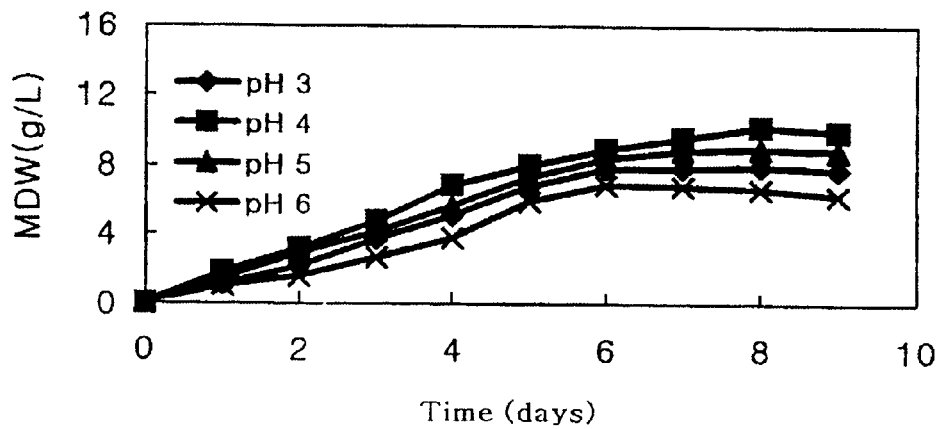
FIG. 5a is a graph showing the MDW at the initial pH in the medium containing no ammonium ion.
Figure 5B:
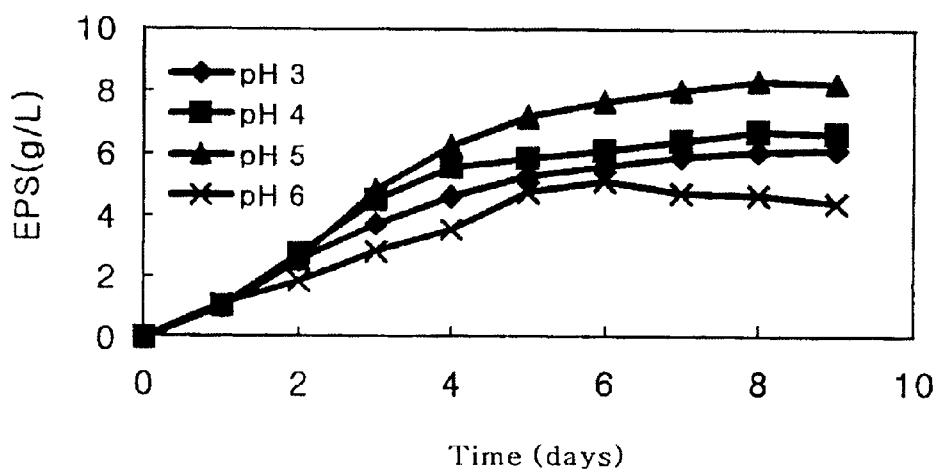
FIG. 5b is a graph showing the EPS at the initial pH in the medium containing no ammonium ion.

After the initial pH conditions in the medium containing no ammonium ion were controlled by 3, 4, 5 and 6, the mycelium was cultured for 9 days; the MDW and EPS were assayed every 12 hours in the same manner as Example 1. The results were summarized in the following FIG. 5a, 5b and table 1.

TABLE 1

| Category  | pH 3 | pH 4  | pH 5 | pH 6 |
|-----------|------|-------|------|------|
| MDW (g/L) | 7.80 | 10.23 | 8.58 | 6.87 |
| EPS (g/L) | 6.14 | 6.72  | 8.25 | 5.10 |

EXAMPLE 5

Effect of Controlled pH in the Medium Containing No Ammonium Ion

Figure 6A:
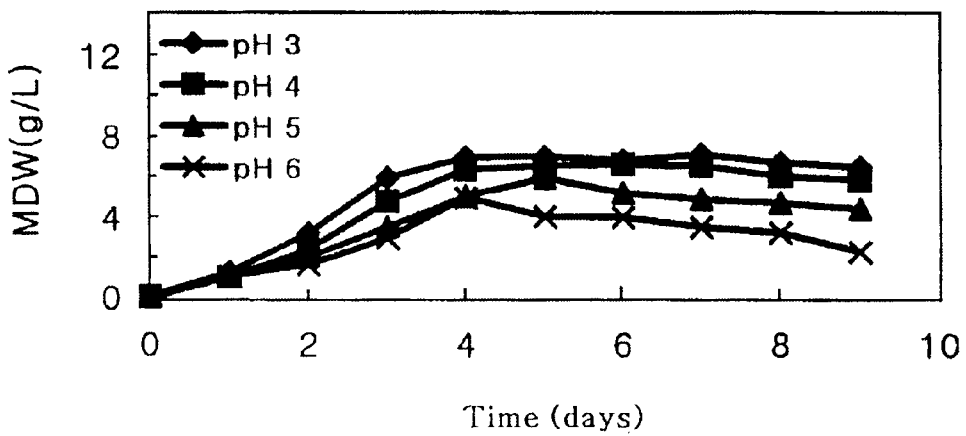
FIG. 6a is a graph showing the MDW when the constant scope of pH is controlled in the medium containing no ammonium ion.
Figure 6B:
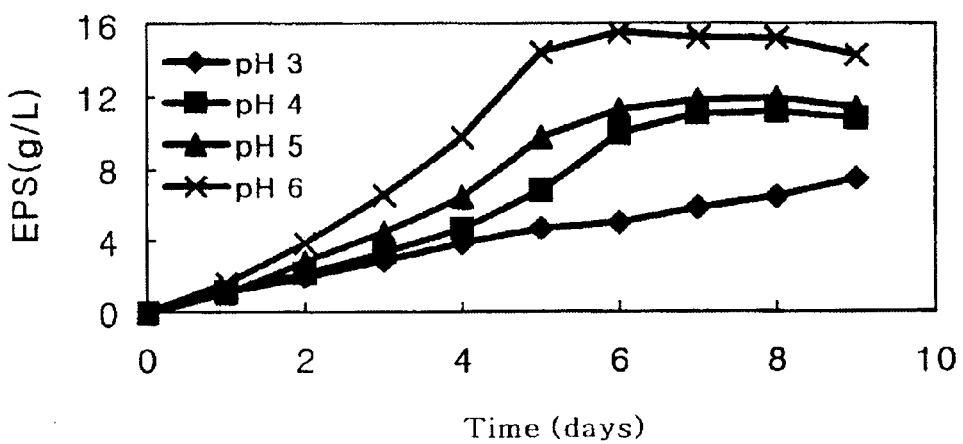
FIG. 6b is a graph showing the EPS when the constant scope of pH is controlled in the medium containing no ammonium ion.

The mycelium was cultured for 9 days in the same manner as Example 4, except for the fact that the pH conditions in the medium were kept constant with the addition of NaOH. The MDW and EPS were assayed every 12 hours in the same manner as Example 1. The results were summarized in the following FIGS. 6a and 6b.

TABLE 2

| Category | pH 3 | pH 4 | pH 5 | pH 6 |
|---|---|---|---|---|
| MDW (g/L) | 7.12 | 6.61 | 6.60 | 5.73 |
| EPS (g/L) | 7.52 | 11.20 | 12.00 | 15.71 |

EXAMPLE 6

Effect of Initial pH in the Medium Containing Ammonium Ion

Figure 7A:
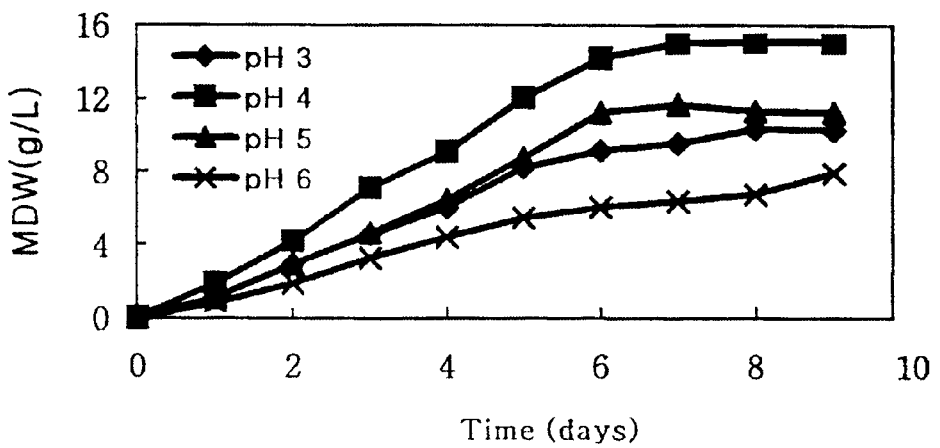
FIG. 7a is a graph showing the MDW at the initial pH in the medium containing ammonium ion.
Figure 7B:
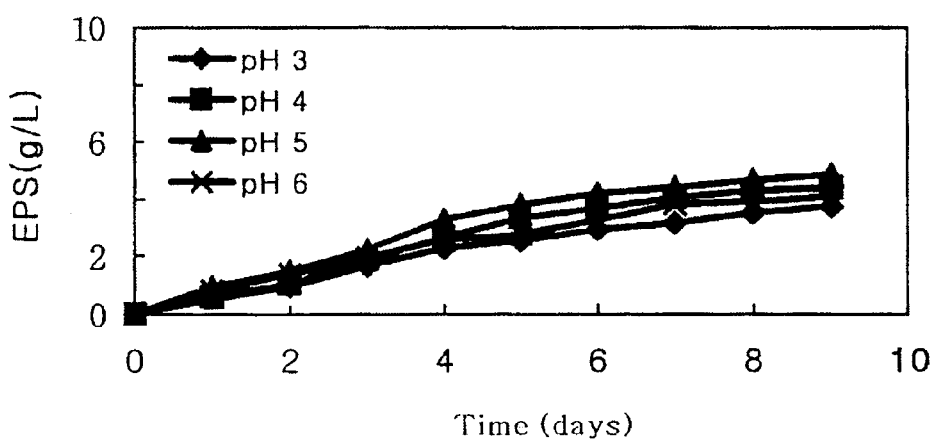
FIG. 7b is a graph showing the EPS at the initial pH in the medium containing ammonium ion.

The mycelium was cultured for 9 days in the same manner as Example 4, except for the fact that 1 g/L of ammonium ion was added to the medium. The MDW and EPS were assayed every 12 hours in the same manner as Example 1. The results were summarized in the following FIGS. 7a, 7b and table 3.

TABLE 3

| Category | pH 3 | pH 4 | pH 5 | pH 6 |
|---|---|---|---|---|
| MDW (g/L) | 10.33 | 15.21 | 11.71 | 7.95 |
| EPS (g/L) | 3.78 | 4.43 | 4.87 | 4.11 |

EXAMPLE 7

Effect of Controlled pH in the Medium Containing Ammonium Ion

Figure 8A:
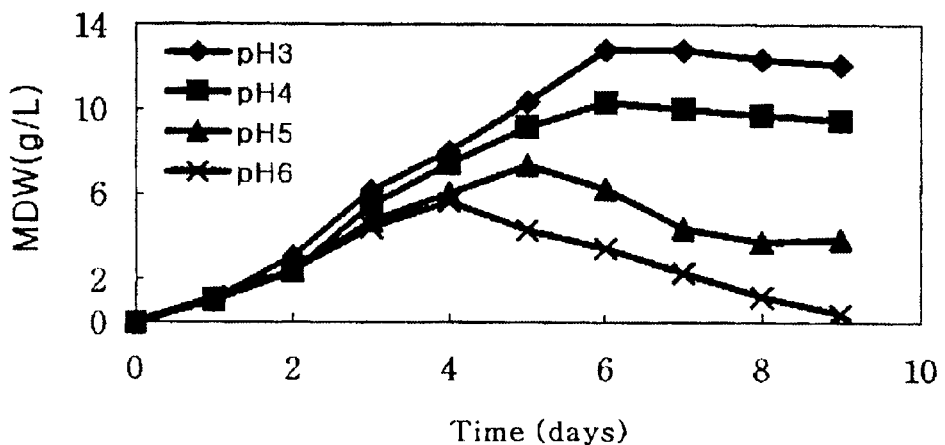
FIG. 8a is a graph showing the MDW when the constant scope of pH is controlled in the medium containing ammonium ion.
Figure 8B:
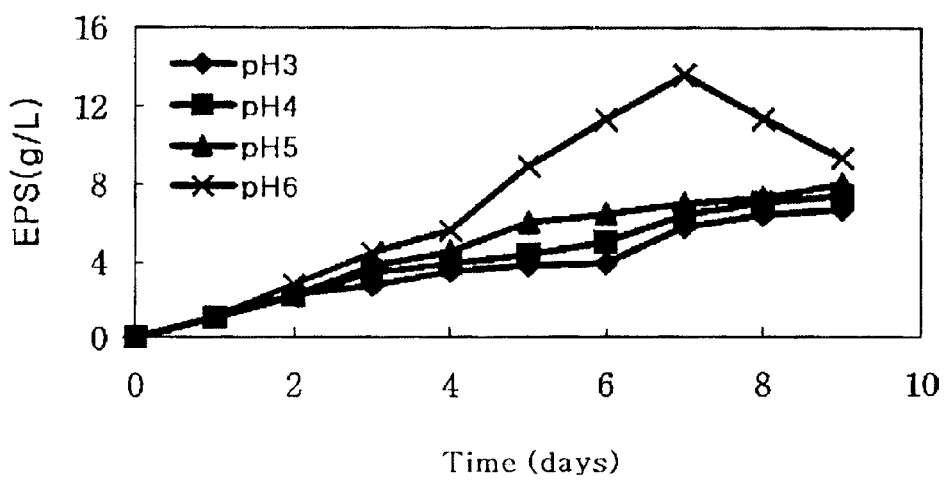
FIG. 8b is a graph showing the EPS when the constant scope of pH is controlled in the medium containing ammonium ion.

The mycelium was cultured for 9 days in the same manner as Example 4, except for the fact that the pH conditions in the medium were kept constant with the addition of NaOH. The MDW and EPS were assayed every 12 hours in the same manner as Example 1. The results were summarized in the following FIGS. 8a, 8b and table 4.

TABLE 4

| Category | pH 3 | pH 4 | pH 5 | pH 6 |
|---|---|---|---|---|
| MDW (g/L) | 12.90 | 10.41 | 7.40 | 5.67 |
| EPS (g/L) | 6.88 | 7.95 | 8.29 | 13.85 |

Examples 4–7 show that when the MDW of both uncontrolled and constant pH control cases in the medium containing ammonium ion was higher than that containing no ammonium ion, while the EPS production in the medium containing no ammonium ion was higher than that containing ammonium ion. The EPS production in the medium containing no ammonium ion was higher than that containing ammonium ion. Further, the MDW at controlled pH was lower than that at uncontrolled pH but the EPS production was high. The maximum EPS production was obtained from the medium containing no ammonium ion at controlled constant pH of 6 and its amount was 15.71 g/L. Further, when the pH condition was constantly maintained at 6, the EPS production in the medium containing no ammonium ion was 1.13 times higher than that containing ammonium ion. However, the EPS production in the medium containing ammonium ion was increased 2.4 times higher than uncontrolled pH cases, while the EPS production in the medium containing no ammonium ion was increased about 2.74 times. Therefore, it was found that the adjustment of pH for the EPS production of *Ganoderma lucidum* was more effective than the cases of adding ammonium ion.

COMPARATIVE EXAMPLE 1

Effect of Initial pH in the Medium Containing No Ammonium Ion

The mycelium was cultured for 9 days in the same manner as Example 4, except for the fact that the pH conditions in the medium were adjusted to 2. The MDW and EPS were assayed every 12 hours in the same manner as Example 1. The results were summarized in the following FIGS. 6a, 6b and table 2. As a result, the maximum level of MDW was 0.8 g/L, while that of EPS was 1.70 g/L.

COMPARATIVE EXAMPLE 2

Effect of Initial pH in the Medium Containing Ammonium Ion

The mycelium was cultured for 9 days in the same manner as Example 6, except for the fact that the pH conditions in the medium were adjusted to 2 and 7. The MDW and EPS were assayed every 12 hours in the same manner as Example 1. The results were summarized in the following FIGS. 6a, 6b and table 2. As a result, the maximum level of MDW was 0.8 g/L, while that of EPS was 1.70 g/L, as shown in the following 5.

TABLE 5

| Category | pH 2 | pH 7 |
|---|---|---|
| MDW (g/L) | 0.93 | 5.21 |
| EPS (g/L) | 1.38 | 3.01 |

COMPARATIVE EXAMPLE 3

Effect of Controlled pH in the Medium Containing Ammonium Ion

The mycelium was cultured for 9 days in the same manner as Example 7, except for the fact that the pH conditions in the medium were adjusted to 2. The MDW and EPS were assayed every 12 hours in the same manner as Example 1. The results were summarized in the following FIGS. 6a, 6b and table 2. As a result, the maximum level of MDW was 3.09 g/L, while that of EPS was 2.13 g/L.

EXPERIMENTAL EXAMPLE 1

Mycelia Morphology (1)

Figure 9:
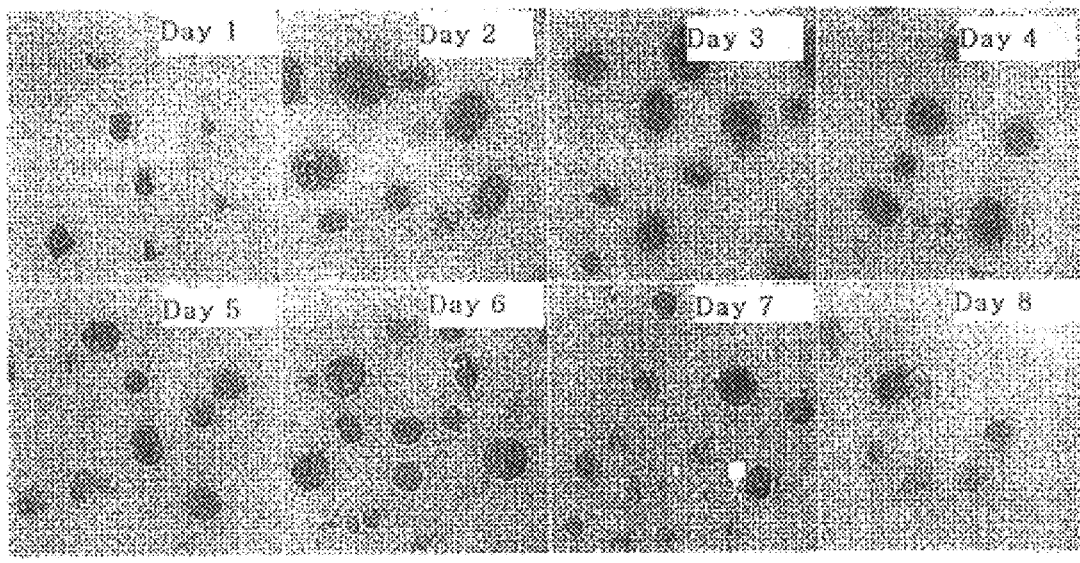
FIG. 9a is a graph showing the time courses on the external form of mycelia during the cultivation of the bistage pH control in the medium containing ammonium ion (the range of pH is shifted from 3 to 6 after 6-hour cultivation).

After the mycelium in the medium containing ammonium ion was cultured at a constant pH 3 for 6 hours, the cultivation was carried out by increasing the pH to 6 using bistage pH control technique, as shown in Example 2. To investigate the mycelial morphology, samples of 1 ml, randomly collected from the fermentor, were fixed with an equivalent amount of fixed solution (13 ml of 40% formaldehyde+5 ml of glacial acetic acid+200 ml of 50% ethanol (v/v) and diluted 20-fold with distilled water. The fixed samples (0.5 ml) were sprayed to a slide glass and dried by air ventilation. The dried samples were washed with absolute alcohol and stained with methylene blue. Image analysis of the fermentation broth was carried out on image capturing board using images obtained from PC (Samsung, Pentium 100)-based Image Analyzer (Optimas Co., U.S.A). The results were summarized in the following FIGS. 9 and 11.

EXPERIMENTAL EXAMPLE 2

Mycelia Morphology (2)

Figure 10:
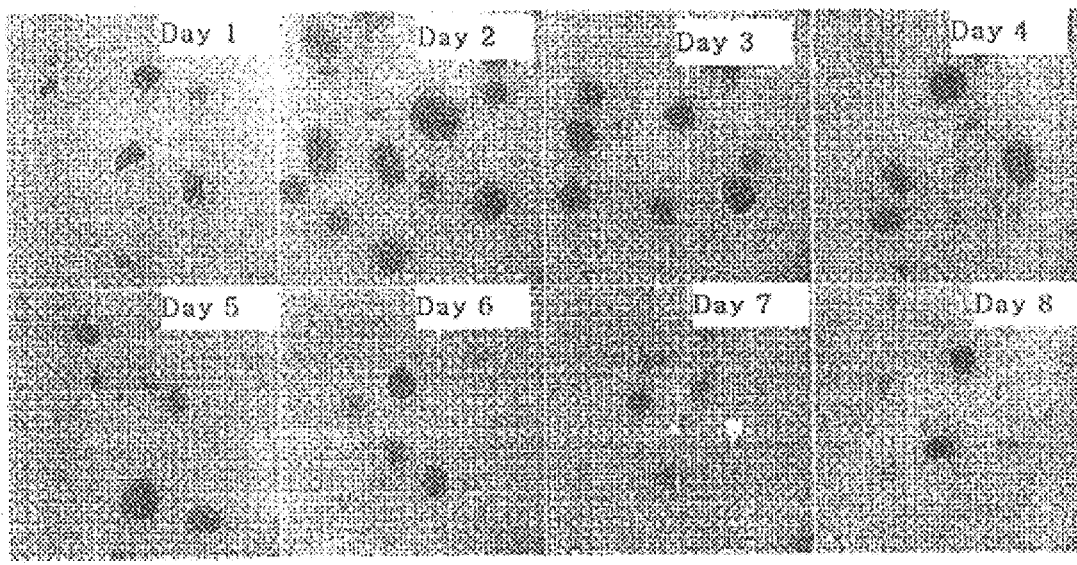
FIG. 10 is a graph showing the time courses on the external form of mycelia during the cultivation of the bistage pH control in the medium containing ammonium ion (the range of pH is shifted from 3 to 6 after 2-day cultivation).

After the mycelium in the medium containing ammonium ion was cultured at a constant pH 3 for 2 days, the cultivation was carried out by increasing the pH to 6 using bistage pH control technique, as shown in Example 3, and then, the mycelial morphology was observed by preparing the samples in the same manner as Experimental example 1, except for the fact that the mycelial morphology in the medium was observed. The results were summarized in the following FIGS. 10~11. Experimental examples 1 and 2 show that regardless of cultivation conditions, the mycelium was grown as pellet forms. When the pH condition was changed after 6-hour cultivation, the mycelium maintained a constant scope of frequency area of pellet forms with appropriate size at the later period. Thereafter, the pellet size and frequency area was decreased from the mid-cultivation period. The pellet size of *Ganoderma lucidum* was enlarged at the initial cultivation but it was gradually reduced with the lapse of time. In particular, after 6-hour cultivation showing the maximum EPS production, the average diameter of pelleted mycelia under the controlled pH control (1.7~2.4 mm) was relatively higher than that of mycelia whose pH condition was controlled after 2-day cultivation (0.99~2.02 mm). It was found that maintaing an appropriate size of pellet forms and constant scope of frequency area may be more advantageous for high EPS production.

Figure 13A:
FIG. 13 is a graph showing the structural changes of mycelia in the presence or absence of ammonium ion during the cultivation of *Ganoderma lucidum*.
Figure 13B:

FIG. 13 also supports the hypothesis on the effect of ammonium ion on cell growth. By adding ammonium ion, the structure of *Ganoderma lucidum* remained unchanged as pellet forms, which could cause limitation of nutrient transport and this was the reason for the decrease in cell growth. With no or a reduced amount of ammonium ion added, the mycelium was turned into the filamentous forms, thus benifitting the cell growth.

EXPERIMENTAL EXAMPLE 3

Figure 11:
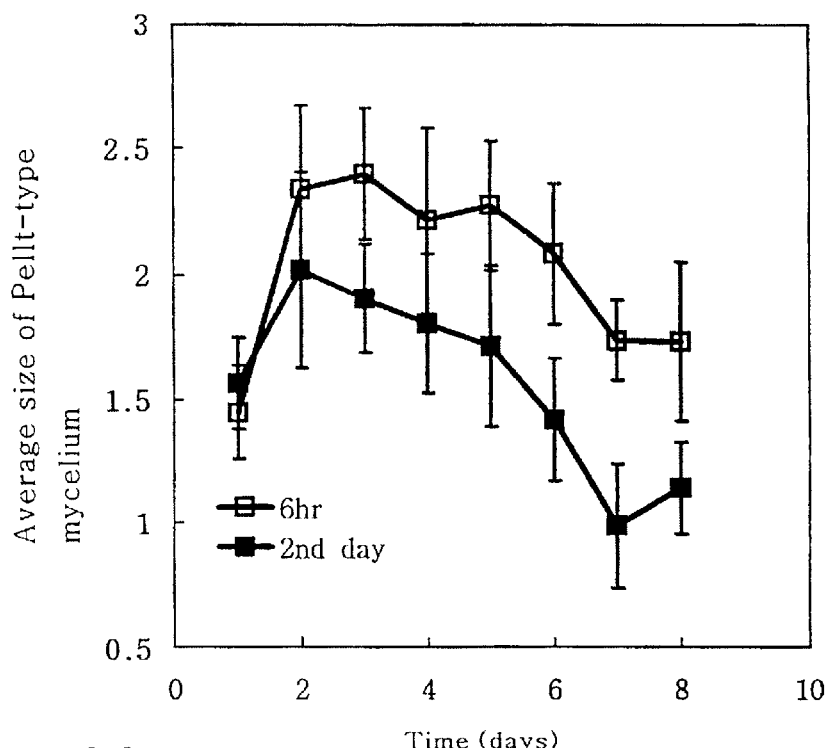
FIG. 11 is a graph showing the time courses on the changes of pellet size under the bistage pH control.
Figure 12:
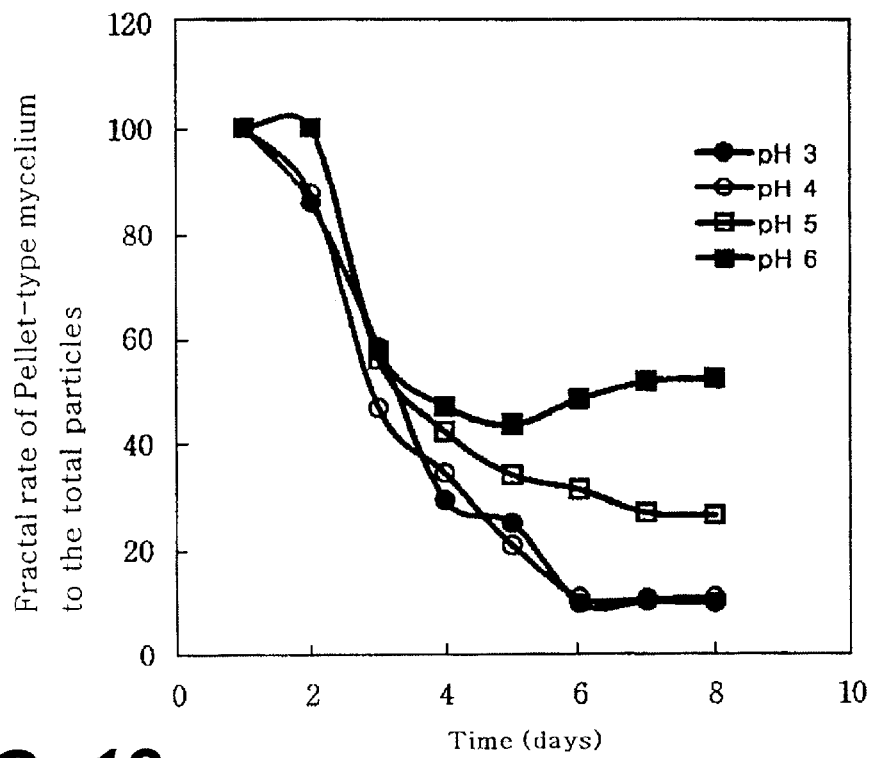
FIG. 12 is a graph showing the number of pellets to the total number of mycelia with time courses under different pH conditions in the medium containing ammonium ion.

Distribution of Pelleted Morphology Present in the Medium Containing Ammonium Ion Under Controlled pH After the mycelium in the medium containing 1 g/L of ammonium ion was cultured with the addition of NaOH under the controlled constant pH, as shown in Example 7, the mycelia morphology was investigated and estimated as fractal rate of pellet forms on the total mycelia in the following FIG. 12. As a result FIG. 11 shows that all pelleted mycelia were present by 100% at the initial cultivation under each of constant pH, but the pellet forms was decreased after 3-day cultivation. From day 6 of cultivation, the pelleted areas at pH 6, pH 5, pH 4 and pH 3 was 48.5%, 24%, 10.4% and 9.3%, respectively. The pelleted area was also reduced by the order of lower pH, that is, pH 6>pH 5>pH 4>pH 3.

It is found that the reduced pH expands the filamentous area, while high pH results in expanding the pelleted area. Therefore, it was deduced that compared to FIG. 8 that the EPS production was maximum at pH 6 and minimum at pH 3, tie mycelial concentration was high for pelleted growth, while the EPS production was high for filamentous growth. Further, the rate of pellet forms in the medium at pH 5 and pH 6, showing a high polysaccharide production was 24~48.5%. It was also found that when the ratios between pellet and filamentous forms were 1:1~3, the EPS production was high.

EXPERIMENTAL EXAMPLES 4

Rheological Parameters (1)

The strain was cultured in the medium (pH 5) containing no ammonium ion. Then, tile rheological parameters of the culture broth, mycelial suspensions and culture filtrate were estimated by a linear minimum multiplication using the following Herschel-Bulkley model every 24 hours for 8 days: consistency index (K), flow index (n) and yield stress ($\tau_y$). The results were summarized in the following table 6.

Mathematical formula 1

$$\tau = \tau_y + K^n$$

where, $\tau$: shear stress, $\tau_y$: yield stress, K: consistency index (Pa·secn), n: flow index (-).

EXPERIMENTAL EXAMPLES 5

Rheological Parameters (2)

The Theological parameters of the culture broth, mycelial suspensions and culture filtrate were estimated in the same manner as Experimental 4, except for the fact that 1 g/L of ammonium ion was added to the medium. The results were summarized in the following table 6.

EXPERIMENTAL EXAMPLES 6

Rheological Parameters (3)

The rheological parameters of the culture broth, mycelial suspensions and culture filtrate were estimated in the same manner as Experimental 4, except for the fact that 7 g/L of ammonium ion was added to the medium. The results were summarized in the following table 6.

TABLE 6

Rheological parameters of the culture broth, mycelial suspensions and culture filtrate in the presence or absence of ammonium ion

|  | Time (day) | Culture broth | | | Mycelial suspensions | | | culture filtrate | | |
| --- | --- | --- | --- | --- | --- | --- | --- | --- | --- | --- |
|  |  | K (PaS$^n$) | n (—) | $\tau_y$ (Pa) | K (PaS$^n$) | n (—) | $\tau_y$ (Pa) | K (PaS$^n$) | n (—) | $\tau_y$ (Pa) |
| Experimental Example 4 | 1 | 0.31 | 0.93 | — | 0.25 | 0.96 | — | 0.28 | 0.89 | — |
|  | 2 | 0.62 | 0.83 | 0.2 | 0.27 | 0.94 | 0.01 | 0.32 | 0.82 | — |
|  | 3 | 1.59 | 0.47 | 0.64 | 0.28 | 0.78 | 0.01 | 0.61 | 0.83 | 0.11 |
|  | 4 | 2.90 | 0.30 | 1.20 | 0.68 | 0.68 | 0.23 | 1.21 | 0.74 | 0.15 |
|  | 5 | 3.10 | 0.33 | 0.98 | 0.96 | 0.58 | 0.32 | 1.52 | 0.25 | 0.15 |
|  | 6 | 3.55 | 0.29 | 1.68 | 1.35 | 0.47 | 0.33 | 1.55 | 0.23 | 0.12 |
|  | 7 | 3.98 | 0.33 | 1.86 | 1.00 | 0.59 | 0.34 | 2.27 | 0.23 | 0.32 |
|  | 8 | 4.40 | 0.40 | 3.3 | 1.01 | 0.57 | 0.34 | 2.50 | 0.24 | 0.34 |
| Experimental | 1 | 0.03 | 0.88 | — | 0.08 | 0.95 | — | 0.07 | 0.91 | — |

TABLE 6-continued

Rheological parameters of the culture broth, mycelial suspensions and culture filtrate in the presence or absence of ammonium ion

| | | Culture broth | | | Mycelial suspensions | | | culture filtrate | | |
|---|---|---|---|---|---|---|---|---|---|---|
| | Time (day) | K (PaS$^n$) | n (—) | $\tau_y$ (Pa) | K (PaS$^n$) | n (—) | $\tau_y$ (Pa) | K (PaS$^n$) | n (—) | $\tau_y$ (Pa) |
| Example 5 | 2 | 0.08 | 0.67 | 0.02 | 0.26 | 0.71 | 0.03 | 0.11 | 0.83 | — |
| | 3 | 1.24 | 0.49 | 0.23 | 0.34 | 0.48 | 0.03 | 0.33 | 0.51 | 0.10 |
| | 4 | 1.46 | 0.50 | 0.30 | 0.45 | 0.62 | 0.13 | 0.34 | 0.53 | 0.11 |
| | 5 | 2.64 | 0.64 | 0.49 | 0.66 | 0.56 | 0.15 | 0.35 | 0.53 | 0.13 |
| | 6 | 2.46 | 0.61 | 0.44 | 0.54 | 0.55 | 0.12 | 0.34 | 0.58 | 0.15 |
| | 7 | 2.40 | 0.60 | 0.35 | 0.36 | 0.57 | 0.01 | 0.39 | 0.53 | 0.15 |
| | 8 | 2.40 | 0.58 | 0.24 | 0.44 | 0.55 | 0.01 | 0.43 | 0.55 | 0.20 |
| Experimental Example 6 | 1 | 0.33 | 0.90 | — | 0.22 | 0.90 | — | 0.27 | 0.93 | — |
| | 2 | 0.48 | 0.83 | 0.01 | 0.26 | 0.81 | — | 0.33 | 0.86 | 0.01 |
| | 3 | 0.54 | 0.8 | 0.06 | 0.32 | 0.76 | 0.02 | 0.36 | 0.84 | 0.03 |
| | 4 | 0.72 | 0.73 | 0.22 | 0.38 | 0.73 | 0.03 | 0.44 | 0.80 | 0.03 |
| | 5 | 0.65 | 0.74 | 0.06 | 0.35 | 0.73 | 0.03 | 0.40 | 0.81 | 0.02 |
| | 6 | 0.70 | 0.72 | 0.09 | 0.43 | 0.70 | 0.02 | 0.52 | 0.75 | 0.03 |
| | 7 | 0.79 | 0.71 | 0.09 | 0.47 | 0.75 | 0.03 | 0.55 | 0.74 | 0.07 |
| | 8 | 0.81 | 0.72 | 0.17 | 0.50 | 0.73 | 0.04 | 0.58 | 0.74 | 0.11 |

The above results indicated that K, consistency index of the culture broth, represented the order of $NH_4^+(-)$>$NH_4^+(1\ g/L)$>$NH_4^+(7\ g/L)$, while flow index with the order of $NH_4^+(7\ g/L)$>$NH_4^+(1\ g/L)$>$N+(-)$. This implies that the rheological properties were greatly influenced by ammonium ion. When the above results are reviewed from the morphological observation of mycelia, K and n values in the medium containing no ammonium ion mainly for filamentous growth of mycelia were 4.40 PaS$^n$ and 0.40(-), respectively, after cultivation. On the other hand, K and n values in the medium containing ammonium mainly for pelleted growth of mycelia were 0.81 PaS$^n$ and 0.72(-), respectively, after cultivation. This explains that K values for filamentous growth of mycelia was significantly higher than those of pelleted growth of mycelia (about 5.5 times), while n values for filamentous growth of mycelia was far less than those of pelleted growth of mycelia (about 6.6 times). More specifically, K values for filamentous mycelia in the same concentration of mycelia was higher than those of pelleted mycelia, while n values for filamentous mycelia was lower than those of pelleted mycelia.

Figure 14:
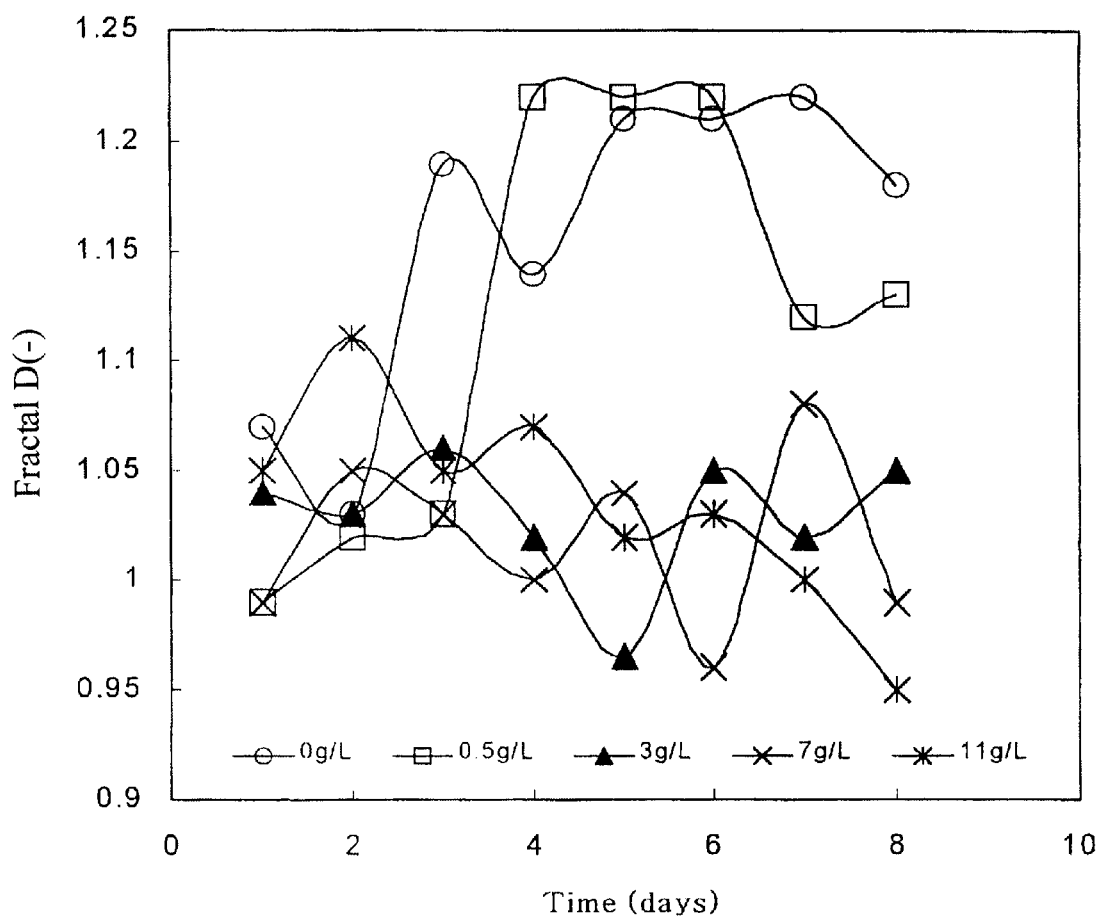
FIGS. 14 and 15 show quantitatively the structural changes of the mycelium with various concentrations of ammonium ion for the batch cultivation of *Ganoderma lucidum*.
Figure 15:
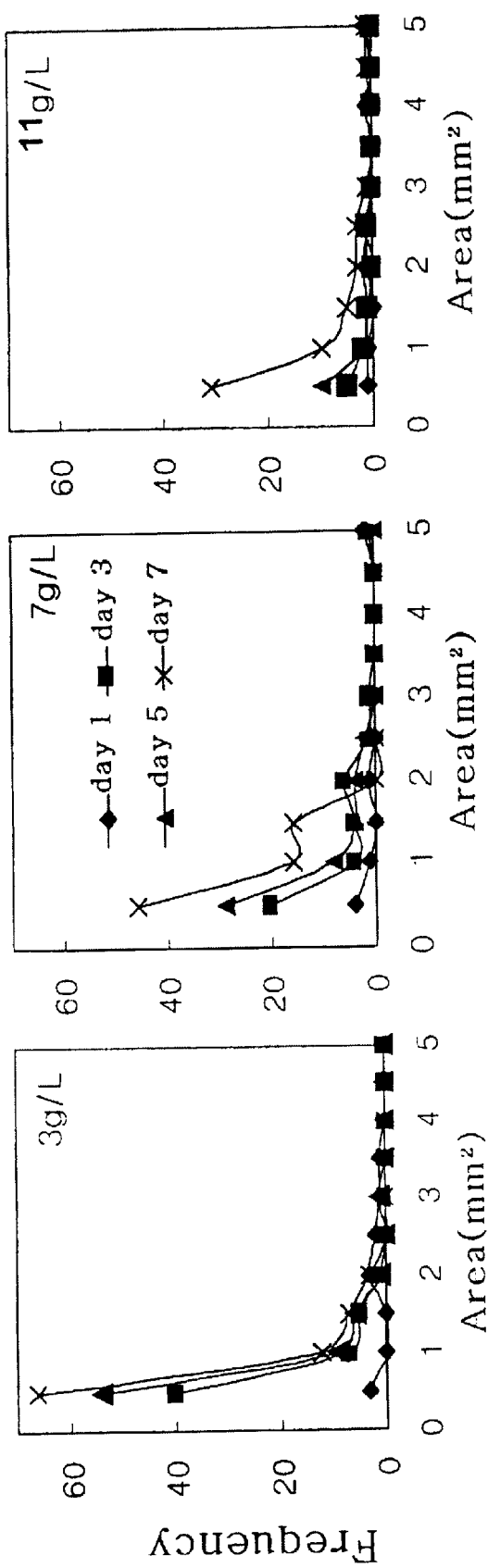

Further, FIGS. 14 and 15 show quantitatively the structural changes of the mycelium with various concentrations of ammonium ion for the batch cultivation of *Ganoderma lucidum*. In a situation where ammonium ion in the medium was low, the mycelium was mainly filamentous, while high fractal dimension (1.1–1.25) was calculated. On the contrary, when ammonium ion was high, a low fractal dimension was calculated, and the mycelium was mainly transformed into pellet forms. FIG. 14 shows the changes of the area frequency of the mycelium with various concentration of ammonium ion for the batch cultivation of *Ganoderma lucidum*. At high ammonium ion concentrations, the frequency rate of the area in relations to pellets (>1 mm$^2$) was lower than at low concentrations (<3 g/L). This is another evidence for decrease of mycelial growth in the medium containing a high concentration of ammonium ion. It was also found that the average size of the pellets (>1 mm$^2$) decreased as the cultivation process continued. Most of the mycelium size in the fermentor fell in the range of 0.5~1.5 mm$^2$, regardless of the cultivation time and ammonium ion concentration. When the size of pellets was enlarged, there should be several limitations due to substrate limitation, increasing shear stress and self-folding activity.

Figure 16A:
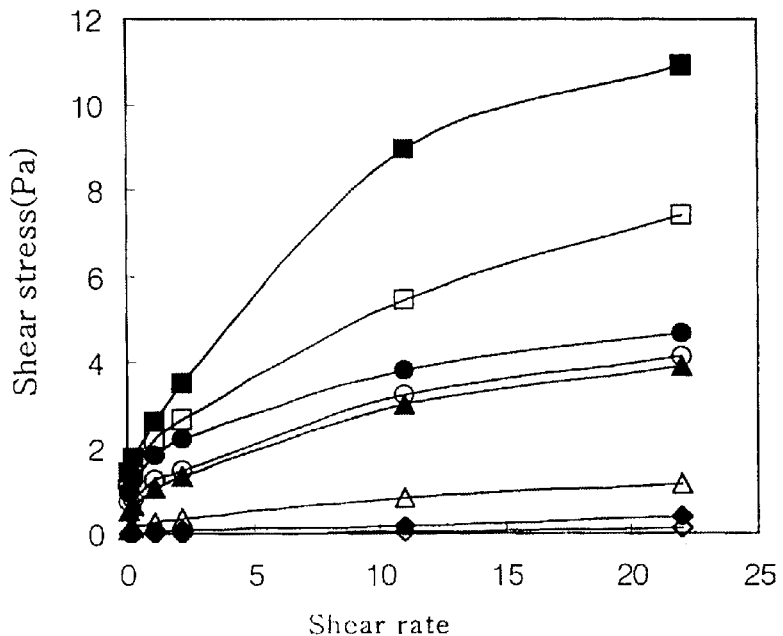
FIGS. 16 and 17 show the rheological parameters of the culture broth and culture filtrate with various concentrations of ammonium ion for the batch cultivation of *Ganoderma lucidum*.
Figure 16B:
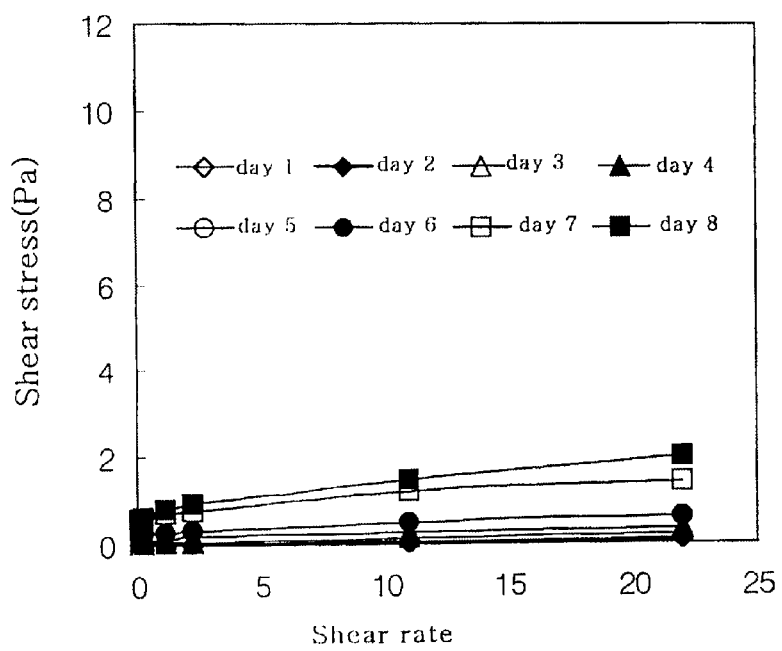
Figure 17A:
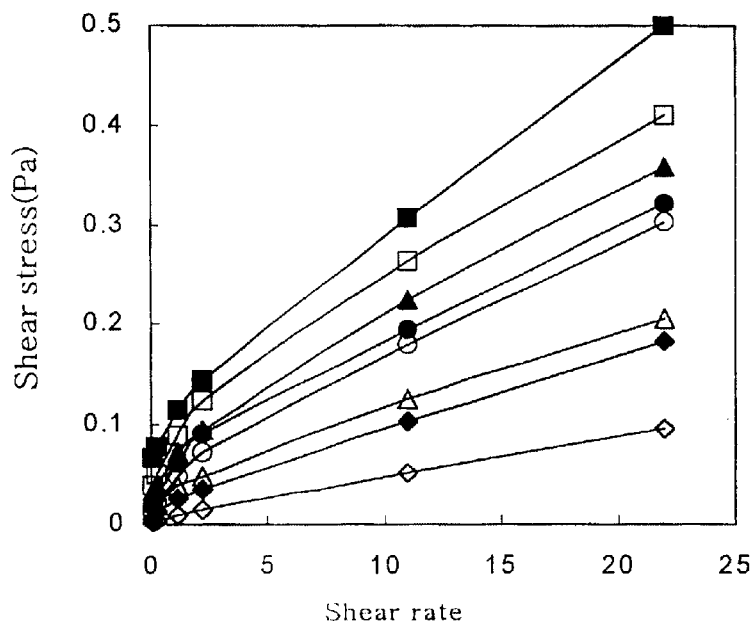
Figure 17B:
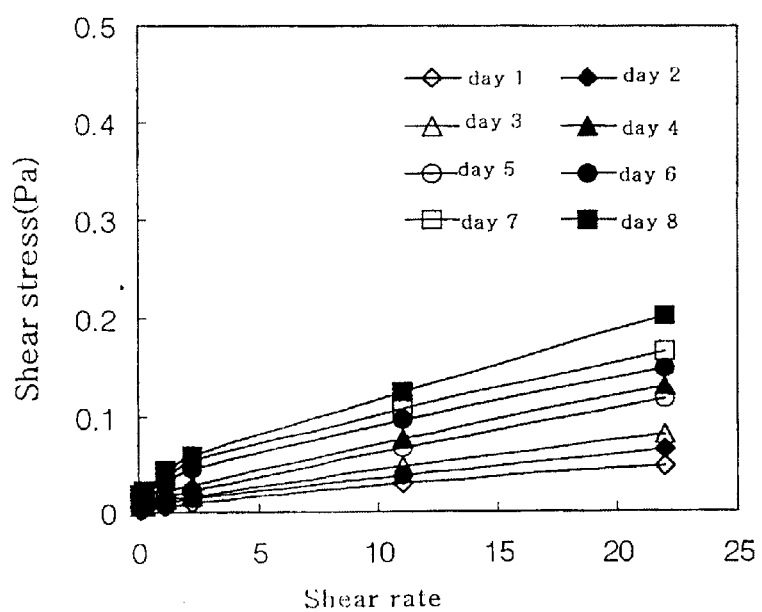

FIGS. 16 and 17 show the effects of ammonium ion concentration on the rheological properties of the filtrate and culture broth during the cultivation. The rheological properties in the medium can affect directly and seriously the performance of the fermentation system in designing, controlling and operating the fermentation process. The shear stress of both the filtrate and culture broth were increased with a non-linear pattern as the shear rate was increased, and this implied that they had the characteristics of the non-Newtonian fluid. In particular, a higher shear stress was observed in the absence of ammonium ion as compared with that in the presence of ammonium ion. This was due to the high mycelial growth and filamentous structure. Further, the shear stress was gradually increased during the cultivation for all cases because of the morphological change of the mycelium in addition to the increase of the cell density.

Meantime, regardless of ammonium ion concentration, the shear diagrams of the culture filtrate were much less affected compared to the culture broth. This means that the rheological property of the culture broth is significantly influenced by mycelial concentration, but not by EPS concentration. It also confirmed that compared to the mycelial morphology in the presence or absence of ammonium ion, the mycelial morphology and concentration are crucial in the changes of flow behavior during the cultivation of *Ganoderma lucidum*. The rheological properties in FIGS. 16 and 17 were well fitted to the Herschel-Bulkley model ($R^2 \geq 0.95$).

Figures 18A, 18B, 18C:
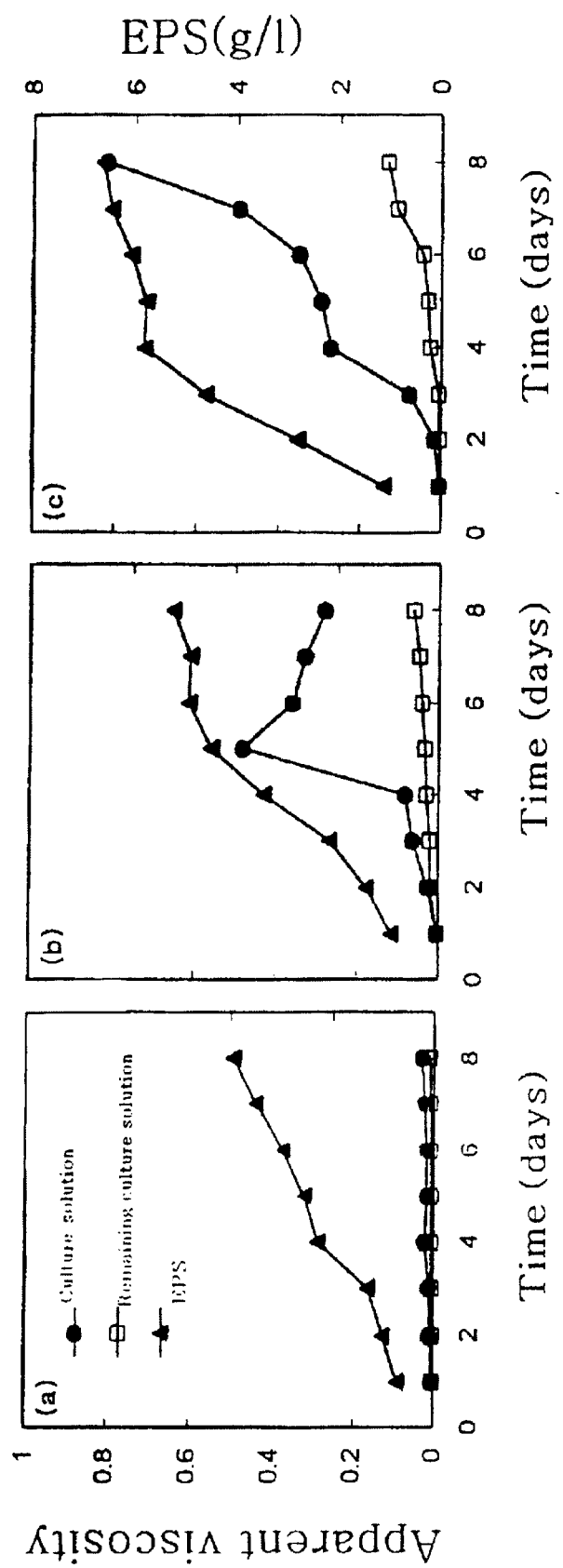
FIG. 18 is a graph showing the effect of ammonium ion on the culture broth and culture filtrate with various concentrations of ammonium ion for the batch cultivation of *Ganoderma lucidum*.

As shown in FIG. 18, in high ammonium ion concentration in the medium (7 g/L), the apparent viscosity of the culture broth and filtrate did not appear to change much by the cultivation time, because of minimum levels of the mycelial growth and EPS production. The continuous increase of the culture filtrate viscosity was observed without adding ammonium ion during the cultivation while yielding the maximum EPS production after 8-day cultivation, and high cell growth was observed by a large increase of the broth viscosity. In 1 g/L of ammonium ion, the apparent viscosity of the culture broth dropped during the fermentation, and the main reason for this fall appeared to be cell lysis. Along with an increase of apparent viscosity of the culture filtrate, continuous EPS production was observed in 1 g/L of ammonium ion or in the absence of ammonium ion, although the mycelial growth was decreased. On the contrary, the EPS production level was not high in the culture when the cells were grown in high ammonium ion concentration. This suggests that an appropriate amount of ammonium ion added in the medium can control the fermentation process towards better stability and higher production.

Meantime, both cell growth and EPS production decreased towards the later periods of cultivation in the case of cultivation at pH 6. This was not observed when pH was controlled at 3. This possibly means that high values of pH, such as 6, negatively affect both cell growth and EPS production, particularly cell growth, in the case of long-term and large-scale cultivations. It can be deduced that maintaining a constant pH of 6 with the increasing amount of NaOH results in cell lysis. This is presumably why EPS production also decreased as a result of cell lysis.

Figure 19:
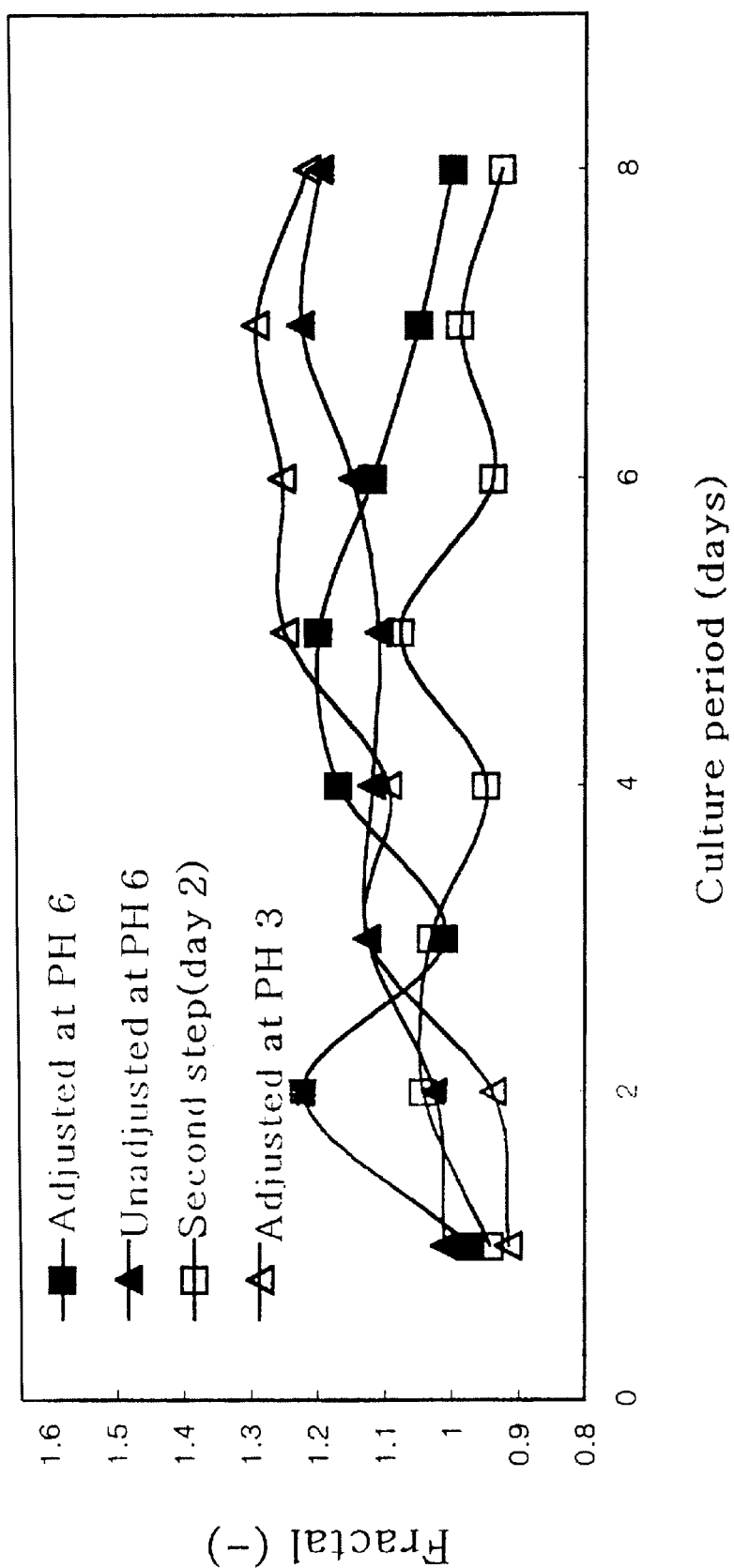
FIGS. 19 and 20 are graphs showing the changes in the size and morphology of mycelia, a critical factor of mycelial cultivation and EPS production, through the time courses of mycelia cultivation under the controlled pH conditions.
Figure 20:
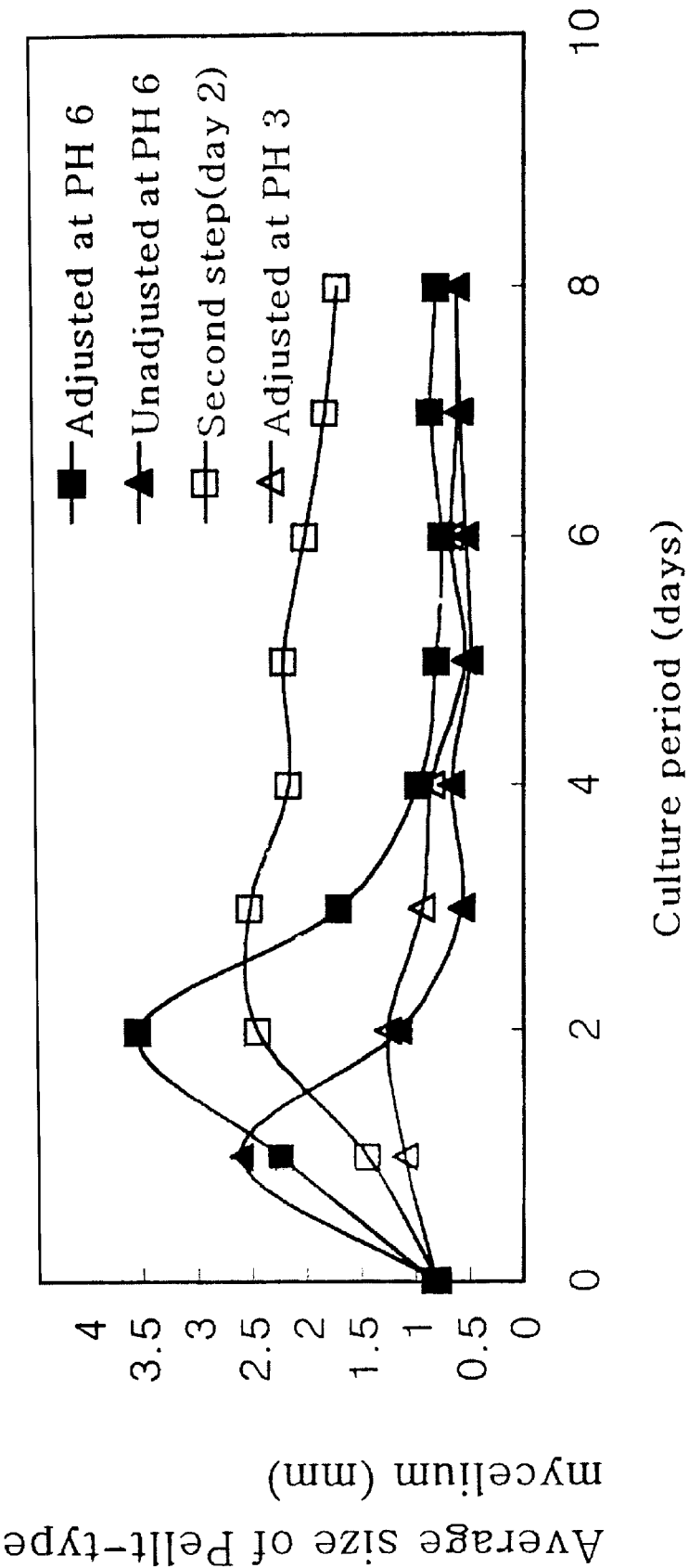

FIGS. 19 and 20 show the effect of pH control on mycerial formation during cultivation, since the size and morphology of the mycelia are critical factors in cultivation and for large-scale production. As shown in FIG. 19, at the controlled pH 3, the smallest pellet size and the highest fractal dimension, which is the favorable morphology for maintaining the mycelial cell growth, compared to those obtained in other cases. This explains why the maximum cell density can be obtained in the case of controlled cultivation at pH 3. In the case of bistage pH control, it is not good for cell growth but advantageous for EPS production. Small pellets can be similarly maintained in uncontrolled and constant pH control cases, compared to very large pellets in bistage pH control. Ammonium ion can affect EPS production as well as cell growth.

Figures 21A, 21B, 21C:
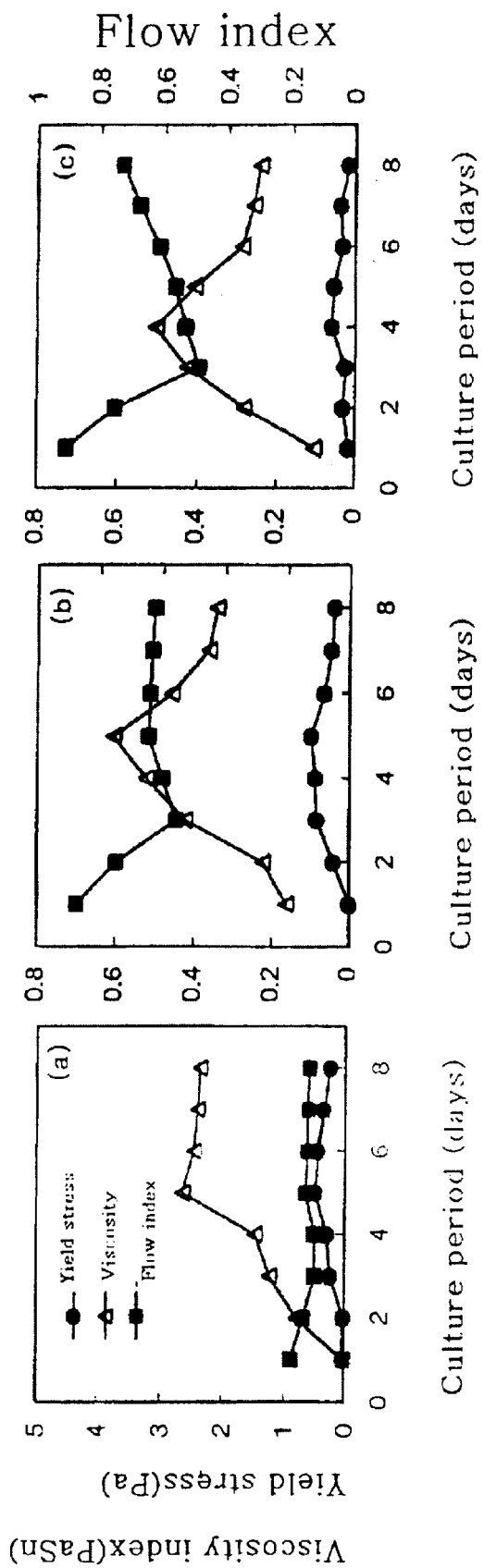
FIG. 21 is a graph showing the changes of viscosity of culture broth in proportion to the changes of the fractal dimension of *Ganoderma lucidum* under the different pH conditions.

Further, as shown in FIG. 21, the Theological parameters were estimated and plotted using a general model with consistency (K) and flow index (n) during the cultivation under three different pH conditions. Values of the consistency index decreased after changing the pH from 3 to 6 and those of the flow index increased by adjusting to pH 6. For uncontrolled pH cultivation, the K values increased gradually with cultivation, showing relatively high values. The results also indicate that controlled pH cultivation (either constant control or bistage control) can reduce the viscosity of the culture broth by controlling the morphology of the mycelium in the pellet-like form. A culture broth containing mycelial pellets exhibits much lower apparent viscosity than one containing filamentous mycelia. The decreased viscosity of the culture broth leads to enhanced oxygen transfer rate and results in improved EPS production. Konig and Schuger also reported that volumetric mass transfer coefficient (Kla) was a factor of 4 to 5 times higher in these pellet suspensions than in the filamentous broth for penicillin fermentation using a tower-loop reactor. According to this invention, the level of D.O. for the uncontrolled pH process sharply decreased from 100% to 5% of air saturation, and remained at about 5% for the cultivation period of 3 days. This indicates oxygen limitation under uncontrolled pH conditions, and D.O. level reached the lowest value of about 60% after 3-day cultivation (data not shown). The highest yield stress was estimated for uncontrolled pH cultivation while the lowest yield stress was estimated for bistage pH control. Bistage pH control affects mycelial morphology during cultivation and results in low viscosity by maintaining more flexible structures than in the case of uncontrolled pH cultivation.

As described above, this invention relates to a process for producing the EPS including bistage pH control technique comprising mycelia cultivation process and EPS production process. According to this invention, the optimized mycelial morphology and Theological properties in the culture media can lead to EPS production in more efficient and stable manner.

What is claimed is:

1. A process for producing exopolysaccharide from submerged mycelial culture of mushroom, wherein it comprises:
    a process for the production of mycelia whose pH conditions in a batch medium are kept constant at 2 to 6 at the initial pH, while adding ammonium ion to the medium; and,
    a process for the production of exopolysaccharides whose pH conditions in a batch medium containing the mycelia are adjusted to 3 to 7.

2. The process for producing exopolysaccharide from submerged mycelial culture of mushroom according to claim 1, wherein said mushroom is *Ganoderma lucidum* belonging to family Polyporaceae.

3. The process for producing exopolysaccharide from submerged mycelial of culture of mushroom according to claim 1, wherein the pH conditions in the medium for said mycelial cultivation are 3 to 4.

4. The process for producing exopolysaccharide from submerged mycelial culture of mushroom according to claim 1 or 3, wherein said batch medium for mycelia cultivation contains 0.01~5 wt. % of ammonium ion.

5. The process for producing exopolysaccharide from submerged mycelial culture of mushroom according to claim 1, wherein the pH conditions in the medium for said EPS production are 5 to 6.

6. The process for producing exopolysaccharide from submerged mycelial culture of mushroom according to claim 1, wherein the pH conditions in the batch media for both mycelial cultivation and EPS production are kept constant.

* * * * *